(12) United States Patent
Melman

(10) Patent No.: US 6,610,276 B2
(45) Date of Patent: Aug. 26, 2003

(54) MULTI-FUNCTIONAL DENTAL COMPOSITION

(76) Inventor: Steven A. Melman, 8909 Iverleigh Ct., Potomac, MD (US) 20854

(*) Notice: Subject to any disclaimer, the term of this patent is extended or adjusted under 35 U.S.C. 154(b) by 0 days.

(21) Appl. No.: 09/758,148

(22) Filed: Jan. 12, 2001

(65) Prior Publication Data

US 2002/0156130 A1 Oct. 24, 2002

(51) Int. Cl.[7] ................................................ A61K 7/16
(52) U.S. Cl. ........................................... 424/57; 424/49
(58) Field of Search ................................ 424/49–88

(56) References Cited

U.S. PATENT DOCUMENTS

| | | | | |
|---|---|---|---|---|
| 2,191,199 A | * | 2/1940 | Hall | 424/57 |
| 3,004,897 A | * | 10/1961 | Shore | 424/57 |
| 3,475,533 A | * | 10/1969 | Mayrand | 424/57 |
| 3,492,131 A | | 1/1970 | Schlatter | 99/141 |
| 3,812,272 A | * | 5/1974 | Linville | 426/380 |
| 3,887,712 A | | 6/1975 | Lover et al. | 424/326 |
| 3,976,765 A | | 8/1976 | Nachtigal | 424/54 |
| 4,012,839 A | | 3/1977 | Hill | 32/15 |
| 4,060,600 A | | 11/1977 | Vit | 424/53 |
| 4,119,711 A | | 10/1978 | Hernestam et al. | 424/54 |
| 4,127,678 A | * | 11/1978 | Burkwall | 426/250 |
| 4,160,821 A | | 7/1979 | Sipos | 424/49 |
| 4,178,363 A | | 12/1979 | Miller, Jr. | 424/49 |
| 4,309,409 A | * | 1/1982 | Coll-Palagos et al. | 424/52 |
| 4,327,079 A | | 4/1982 | Aoki | 424/57 |
| 4,357,318 A | * | 11/1982 | Shah et al. | 424/52 |
| 4,420,471 A | * | 12/1983 | Elton et al. | 424/49 |
| 4,460,565 A | * | 7/1984 | Weststrate et al. | 421/52 |
| 4,610,871 A | | 9/1986 | Lynch | 424/48 |
| 4,636,382 A | | 1/1987 | Hernestam et al. | 424/54 |
| 4,784,862 A | * | 11/1988 | Wotherspoon | 426/103 |
| 4,806,173 A | * | 2/1989 | Toukan | 134/42 |
| 4,902,497 A | * | 2/1990 | Crisanti et al. | 424/52 |
| 4,913,895 A | * | 4/1990 | Miyake et al. | 424/57 |
| 5,122,365 A | * | 6/1992 | Murayama | 424/49 |
| 5,143,720 A | * | 9/1992 | Lopes | 424/55 |
| 5,240,415 A | | 8/1993 | Haynie | 433/216 |
| 5,296,217 A | * | 3/1994 | Stookey | 424/57 |
| 5,376,374 A | * | 12/1994 | Zelaya | 424/195.1 |
| 5,460,802 A | * | 10/1995 | Asami et al. | 424/49 |
| 5,603,921 A | | 2/1997 | Bowen | 424/49 |
| 5,618,518 A | * | 4/1997 | Stookey | 424/57 |
| 5,645,428 A | | 7/1997 | Yarborough | 433/215 |
| 5,648,064 A | | 7/1997 | Gaffar et al. | 424/53 |
| 5,707,610 A | * | 1/1998 | Ibsen et al. | 424/49 |
| 5,942,211 A | * | 8/1999 | Harper et al. | 424/49 |
| 5,980,641 A | * | 11/1999 | Jakubowski | 134/1 |
| 6,063,364 A | * | 5/2000 | Makos | 424/49 |
| 6,149,895 A | | 11/2000 | Kutsch | 424/53 |
| 6,379,725 B1 | * | 4/2002 | Wang et al. | 426/72 |
| 6,387,858 B1 | * | 5/2002 | Shah et al. | 510/161 |

FOREIGN PATENT DOCUMENTS

| | | | |
|---|---|---|---|
| CN | 1175398 | * | 3/1998 |
| CN | 1175406 | * | 3/1998 |
| CN | 1259340 | * | 7/2000 |
| EP | 585509 A1 | * | 3/1994 |
| WO | 95/12380 | * | 5/1995 |

OTHER PUBLICATIONS

Edward E. Mueller, "Colorants for Foods, Drugs, and Cosmetics", Kirk–Othmer Encyclopedia of Chemical Technology, 3rd Edition, vol. 6, pp. 561–595. © 1979.

* cited by examiner

Primary Examiner—Shep K. Rose
(74) Attorney, Agent, or Firm—Corinne Marie Pouliquen

(57) ABSTRACT

This invention relates to novel dental compositions and methods for preventing dental plaque and carie formation and generally for inhibiting tooth decay and brightening/whitening teeth. The compositions of this invention comprise organic acids such as acetic acid and salts thereof which can be combined with pharmaceutically acceptable carriers or diluents to be administered in the form of conventional dental compositions. The compositions of the present invention also preferably contain sodium hexametaphosphate.

4 Claims, No Drawings

MULTI-FUNCTIONAL DENTAL COMPOSITION

FIELD OF THE INVENTION

The present invention relates generally to an oral hygiene product. More particularly, the present invention relates to a dental composition such as a tooth paste, cream, gel or dentifrice, a mouth wash or rinse, a dental pack, or dental floss. Specifically, the invention relates to multi-functional dental products containing acetic acid.

BACKGROUND OF THE INVENTION

Bacterial aggregation on the teeth is known as plaque and causes dental caries, gingivitis, periodontitis and other gum diseases. A variety of microorganisms are present in the oral cavity. These range from the natural flora of the host to pathogenic species. Among these microorganisms are the gram-positive rods associated with the formation of plaque (a dense, enamel-adherent, microorganism-containing polysaccharide matrix). Specific areas, including periodontal and subgingival spaces, and interpapillary spaces of the tongue present environments that harbor bacteria. These spaces are difficult to reach by tooth brushing, and are only moderately affected by standard mouthwashes. Mechanical methods have been used for some time for the prevention of dental plaque but have not generally achieved sufficient results. Studies have shown that mechanical methods such as the use of dental floss and inter-space brushes do not efficiently eliminate plaque. The persistence of these microorganisms in such environments greatly increases the risk of calculus and plaque build up and carie formation, which in turn presents the danger of gingival inflammation and periodontal disease. Thus chemical plaque control as a substitute or supplement to mechanical methods is sought.

U.S. Pat. No. 4,636,382 describes morpholino compounds which are useful for the inhibition or removal of dental plaque. The '382 patent also discloses that a wide variety of chemical and biological agents have been suggested for the inhibition of plaque, such as penicillin, chlorhexidine, 8-hydroxyquinoline and ethylenediamine tetraacetate. However, many of these chemical and biological agents are described as exhibiting insignificant effects and often causing serious side effects. U.S. Pat. No. 4,610,871 describes the use of monoalkyl or dialkyl ethers of dianhydrohexitols to inhibit the formation of plaque and calculus on teeth. U.S. Pat. No. 4,178,363 describes the use of n-undecylenic fatty acid or a calcium or zinc salt thereof for reducing dental plaque and infections of the teeth and gums. U.S. Pat. No. 4,119,711 describes spiro 1-(hydroxyalkyl)-piperidino derivatives which have efficacy in reducing the formation of plaque. U.S. Pat. No. 3,976,765 describes bis-biguanido hexanes in combination with nonionic surfactants and certain foam stabilizers for use in a variety of oral preparations. Additionally, U.S. Pat. No. 3,887,712 discloses that alexidine dihydrofluoride is useful in the treatment of dental plaque, calculus, gingivitis and related periodontal diseases. U.S. Pat. No. 4,160,821 discloses that a glycerine solution of zinc chloride or other acceptable zinc salts provides effective therapy for gingivitis when applied to the gingivae and teeth. U.S. Pat. Nos. 6,149,895; 5,240,415; 5,648,064; and 5,645,428 disclose teeth-bleaching compositions having as active ingredient hydrogen peroxide. U.S. Pat. No. 4,012,839 teaches a technique of disinfecting caries-infected or potentially caries-infected dental tissue with silver nitrate, silver thiocyanate or its complexes. U.S. Pat. No. 4,060,600 teaches a method of treating teeth in dentistry, for the prevention of calculus, removal of caries, and dissolution of plaque, comprising applying an aqueous solution containing a hypochlorite of an alkali and/or alkaline earth metal, and an amino compound capable of forming water-soluble non-mucous irritating N-chloro and/or N-dichloro derivatives thereof to the teeth. U.S. Pat. No. 4,327,079 provides a dentifrice composition containing synthetic hydroxyapatite powder which is neutral or weakly alkaline or contains 0.1 to 20% by weight of NaCl and/or KCl and 0.003 to 3% by weight of $MgCl_2$ as useful for fortifying a surface of a tooth, promoting remineralization of the surface of the tooth and eliminating plaque from the tooth.

While it is thus clear that a variety of approaches have been tried in the past, efforts continue toward finding improved means for brightening teeth and reducing and/or eliminating plaque without many of the side effects associated with the prior art, such as discoloration of teeth or tongue, desquamation and soreness of oral mucosa, objectionable taste, toxicity and imbalance of the oral flora. For example, chlorhexidine is know to stain teeth, and has been know to cause tissue necrosis of the tongue and gums which may persist in tissue. Also, while chlorhexidine has good antibacterial qualities, it has poor cleansing qualities. Hydrogen peroxide has poor antibacterial properties but works very well by using bursts of oxygen to flush out debris and cleanse.

SUMMARY OF THE INVENTION

This invention relates to the treatment of teeth and gums. An object of the invention is to provide a composition for treating teeth, for the removal of plaque and caries, and for the prevention of the build-up of calculus.

It is an object of the present invention to provide a novel composition which is useful in cleansing and brightening teeth and in the treatment of plaque and gingivitis without many of the adverse side effects associated with other compositions. It is another object of this invention to provide dental compositions which would cause little or no ecological imbalance of the oral flora. It is a further object of this invention to provide a composition comprising a combination of acetic acid and conventional tooth paste ingredients wherein this composition possesses improved anti-plaque, anti-gingivitis, and cleansing activity.

Another object is to provide a method for treating teeth which removes plaque and caries, without damaging the teeth.

Yet another object is to provide a method of treating teeth by dissolving away or dispersing plaque and caries, thus essentially eliminating the need for mechanical removal.

The composition of the present invention can be delivered in common dental products such as tooth pastes or dentifrices, tooth powders, mouthwashes, dental floss, toothpicks, chewing gum and the like.

The dental product of the present invention cleans and brightens/whitens teeth. It is also suitable for the treatment of gum disease. It is equally well suited for the prevention of caries, calculi and tartar formation as well as to help remove them.

By addition of a suitable carrier, e.g., a thickening agent, such as colloidal silica, to form a paste, the solution may be more readily applied with an applicator such as a toothbrush or the like. Such a paste may contain other conventional additives such as an abrading agent such as calcium phosphate, calcium carbonate, magnesium carbonate, etc. The dentifrice composition of the present invention can include various other additives which are commonly employed in dentifrices and are well known in the art.

The composition of the present invention need not to be in semi-solid or solid form, i.e., paste or powder, but can be equally used as a solution to be brought adequately into contact with the teeth for a sufficient period of time to enable the plaque and caries to be dissolved and the teeth to be cleansed and brightened, e.g., as a conventional mouth rinse or mouth wash.

The present invention also includes a method of treating teeth in dentistry, for the prevention of calculus, and/or the removal of caries, and/or the dissolving of plaque, and/or brightening/whitening teeth, comprising bringing into contact with the teeth a composition comprising acetic acid and preferably, a preparation containing conventional tooth paste or dentifrice ingredients. Conventional ingredients include, but are not limited to colorants, abrasives and polishing agents, flavoring agents, sweeteners, buffers, diluents, surfactants, gum, sodium fluoride, glycerol, chelating agents, and other ingredients well-known as dental additives and carriers.

The preferred dental product of the present invention contains acetic acid. Preferably the composition also contains sodium hexametaphosphate. By way of example, a suitable acetic acid solution is about 1% to 2%. In accordance with the scope of this invention, the pH of the solution should be maintained between 4 and 7 inclusive. Preferably, the pH is 5.5±1, more preferably, the pH is about 5.0. In order to maintain the preferred pH range it is desirable to add a buffer system to the dental composition. Such a buffer is preferably compatible with the preferred compounds, that is, it should not have any negative effect on same, and should be non-toxic.

DETAILED DESCRIPTION OF THE INVENTION

The dental product of the present invention is a tooth gel/dentifrice that cleans and brightens/whitens teeth. However, the instant dental product can also be a mouth wash, a paste, a gel, a dental pack, or dental floss. It may also be used to treat gum disease. It is equally well suited to prevent caries, calculi and tartar formation as well as to help remove them.

The dental product of the present invention contains acetic acid. Preferably the composition also contains sodium hexametaphosphate.

Examples of some acids which may be used according to the present invention instead of or in addition to acetic acid are phosphoric acid, boric acid, hydrochloric acid, maleic acid, benzoic acid, citric acid, lactic acid, malic acid, oxalic acid, tartaric acid, succinic acid, glutaric acid, glycolic acid, gentisic acid, valeric acid, gallic acid, beta-resorcylic acid, acetyl salicylic acid, salicylic acid, perchloric acid, barbituric acid, sulfanilic acid, phytic acid, p-nitro benzoic acid, stearic acid, palmitic acid, oleic acid, myristic acid, lauric acid ethylenediaminetetraacetic acid (EDTA), ethylene glycol-bis{beta-aminoethyl ether}-N,N,N',N'-tetraacetic acid, and diethylenetriamine pentaacetic acid and the like. The most preferred salts are those of acetic acid but any pharmaceutically acceptable salts of the above acids are equally suitable In the compositions of this invention, acetic and other organic acids are present preferably in an amount ranging from about 0.001% to about 5.0% by weight of the total composition; more preferably from about 0.01% to about 3.0%; most preferably from about 0.05% to about 1.2%, even more preferably from about 0.08 to about 1.0%.

The desired pH range achieved by the content of acid in the composition is between 4 and 7 inclusive. Preferably, the pH is 5.5±1, more preferably, the pH is about 5.0. In order to maintain the preferred pH range in some occasions it can be desirable to add a buffer system to the dental composition. The selection of the buffer is well known in the art and the buffer is preferably compatible with the other ingredients, that is, it should not have any negative effect on same, and should be non-toxic.

The present invention successfully cleans and brightens teeth while inhibiting and reducing the growth of plaque bacteria, which is achieved when acetic acid or other equivalent organic acid is utilized in combination with conventional dental ingredients in effective concentrations to treat the oral cavity. Small quantities of this unexpectedly simple and nevertheless active component is required to obtain effective inhibition of plaque and other bacteria. Since low quantities of active component can be used in the compositions of this invention, the side effects associated with use of the present invention is correspondingly reduced or eliminated.

Microorganisms that may be eliminated by the present composition and methods include but are not limited to *Candida albicans, Cryptococcus neoformans, Aspergillus fumigatus, Candida krusei, Candida parapsilosis, Candida tropicalis,* Malassezia species, *Trichophyton rubrum,* Epidermophyton species, Microsporum species, Sporothrix species, *Blastomyces dermatitidis, Coccidiodes immiitis, Histoplasma capsulatum, Staphylococcus aureus, Streptococcus faecalis, Escherichia coli, Pseudomonas aeruginosa, Enterobacter aerogenes, Klebsiella pneumoniae, Staphylococcus epidermis, Zanthomonus maltrophilia, Acinetobacter, Enterobacter cloacae, Serratia marscens,* Listeria, Monocytogenes, *Enterococcus faecalis, Streptococcus pyogenes, Streptococcus pneumonia, Viridans streptococci, Haemophilus influenzae, Proteus mirabills, Proteus vulgaris* and *Bacterioides fragilis* among many others.

In one form of this invention, the composition may be a liquid such as a mouthwash or rinse. In such a composition the vehicle is typically a water-alcohol mixture. Generally the ratio of water to alcohol is in the range of from about 1:1 to about 20:1, preferably about 3:1 to about 20:1 and most preferably about 3:1 to about 10:1 by weight. The most preferred mouthwash or mouth rinse compositions comprise from 0 to about 30% by weight alcohol, such as ethanol. The total amount of water-alcohol composition in a mouthwash composition is typically in the range from about 70% to about 99.9% by weight of the composition. The pH value of such a mouthwash composition is generally from about 4.0 to about 7.0 and preferably from about 5 to about 6.5. A pH below 4 would be irritating to the oral cavity. A pH greater than 7 would result in an unpleasant feel.

Oral liquid compositions may also contain surface active agents in amounts up to about 5% and fluorine-providing compounds in amounts up to about 2% by weight of the composition.

The composition also comprises chelating agents, including but not limited to, ethylenediaminetatraacetic acid, edetate sodium, edetate disodium, edetate trisodium, edetate calcium disodium, deferoxamine, ditiocarb sodium, aluminum salts, citric acid-sodium salt, gluconic acid-sodium salt, tartaric acid, sodium hexametaphosphate, anthranilic acid, phosphonate, polyacrylic acid, alkyl-diamine polyacetic acids and salts, penicillamine, pentetic acid, succimer and trientine. The preferred chelator is sodium hexametaphosphate. These chelators are especially useful in preventing and dissolving calculus build-up.

Surface active agents are organic materials which afford complete dispersion of the composition throughout the oral cavity. The organic surface active material may be non-ionic, amphoteric, or cationic.

Preferred non-ionic surface active agents include condensates of sorbitan mono-oleate with from 20 to 60 moles of ethylene oxide (e.g., "Tweens" a trademark of ICI United States, Inc.), condensates of ethylene oxide with propylene oxide and condensates of propylene glycol ("Pluronics" a trademark of BASF-Wyandotte Corp.).

Other suitable non-ionic surfactants are the condensation products of an alpha-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resulting surfactants are heteric polymers having a molecular weight in the range of about 400 to about 1600 and containing 40% to 80% by weight of ethylene oxide, with a alpha-olefin oxide to polyhydric alcohol mole ratio in the range of about 1:1 to 1:3.

Amphoteric surfactants useful in the present invention are zwitterions having the capacity to act as either an acid or a base. They are generally non-irritating and non-staining. Non-limitative examples of suitable amphoteric surfactants include cocoamidopropyldimethylsultaine and cocodimethylbetaine (commercially available from Lonza Chem. Co. under the trade-names Lonzaine CS and Lonzaine 12C, respectively).

Cationic surface active agents are molecules that carry a positive charge such as the quaternary ammonium compounds and are well know to those of skill in the art.

A fluorine providing compound may be present in the oral compositions of this invention. These compounds may be slightly water soluble or may be fully water soluble and are characterized by their ability to release fluoride ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono-and difluorophosphate and fluorinated sodium calcium pyrophosphate.

In an oral liquid composition such as a mouthwash, the fluorine providing compound is generally present in an amount sufficient to release up to about 0.15%, preferably about 0.001% to about 0.05%, fluoride by weight of the composition.

The compositions of this invention may be substantially solid or pasty in character such as dental cream, toothpaste, toothpowder or chewing gum. Such solid or pasty oral compositions may also contain polishing materials. Typical polishing materials are abrasive particulate materials having particle sizes of up to about 20 microns. Nonlimiting illustrative examples include water-insoluble sodium metaphosphate, potassium metaphosphate, tricalcium phosphate, dehydrated calcium phosphate, anhydrous dicalcium phosphate, dicalcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 99% by weight of the composition. Preferably, such materials are present in amounts from about 20% to about 75% in toothpaste, and from about 70% to about 99% in toothpowder.

In clear gels, a polishing agent of colloidal silica and alkali metal aluminosilicate complexes are preferred since they have refractive indices close to the refractive indices of gelling agent liquid systems commonly used in such dentifrices.

The compositions of the present invention may additionally contain sweeteners, flavorants and colorants.

In the instance where auxiliary sweeteners are utilized, the present invention contemplates the inclusion of those sweeteners well known in the art, including both natural and artificial sweeteners. Water-soluble sweetening agents such as monosaccharides, disaccharides and polysaccharides such as xylose, ribose, glucose, mannose, galactose, fructose, dextrose, sucrose, maltose, partially hydrolyzed starch, or corn syrup solids and sugar alcohols such as sorbitol, xylitol, mannitol and mixtures thereof. Without limiting to these examples, water-soluble artificial sweeteners such as the soluble saccharin salts, i.e., sodium, or calcium saccharin salts, cyclamate salts, acesulfame-K and the like, and the free acid form of saccharin are equally suitable. Other sweeteners such as dipeptide based sweeteners such as L-phenylalanine methyl ester and materials described in U.S. Pat. No. 3,492,131 (herein incorporated by reference) and the like are equally suitable.

In general, the amount of sweetener will vary with the desired amount of sweetness selected for a particular composition. This amount will normally be 0.01% to about 40% by weight. The water-soluble sweeteners are preferably used in amounts of about 5% to about 40% by weight, and most preferably from about 10% to about 20% by weight of the final composition. In contrast, the artificial sweeteners described are preferably used in amounts of about 0.005% to about 5.0% and most preferably about 0.05% to about 2.5% by weight of the final composition. These amounts are ordinarily necessary to achieve a desired level of sweetness independent from the flavor level achieved from flavorants.

Suitable flavorings include both natural and artificial flavors, and mints such as peppermint, citrus flavors such as orange and lemon, artificial vanilla, cinnamon, various fruit flavors and the like. In one embodiment the flavoring agent comprises cinnamon-clove beads. Such beads can be additionally filled with fillers consisting of inert materials or medicinal agents such as vitamins or antibacterial agents. Both individual and mixed flavors are contemplated. The flavorings are generally utilized in amounts that will vary depending upon the individual flavor, and may, for example, range in amounts of about 0.1% to about 6% by weight of the final composition.

The colorants useful in the present invention, include the pigments which may be incorporated in amounts of up to about 2% by weight of the composition. Also, the colorants may include other dyes suitable for food, drug and cosmetic applications, and known as FD & C dyes and the like. The materials acceptable for the foregoing uses are preferably water-soluble. Illustrative examples include the indigo dye, known as FD & C Blue No. 2, which is the disodium salt of 5,5-indigotindisulfonic acid. Similarly, the dye known as FD & C Green No. 1, comprises a triphenylmethane dye and is the monosodium salt of 4-[4-N-ethyl-p-sulfobenzyl amino) diphenylmethylene]-[1-(N-ethyl-N-p-sulfoniumbenzyl)-2, 5-cyclohexadie nimine]. A full recitation of all FD & C and D & C colorants useful in the present invention and their corresponding chemical structures may be found in the Kirk-Othmer Encyclopedia of Chemical Technology, 3rd Edition, in Volume 6, at pages 561–595, which text is accordingly incorporated herein by reference.

A medicated dental floss for controlling the bacterial activity associated with gingivitis is also contemplated. The floss incorporates acetic acid which, as a result of the flossing action, is deposited to the inter-dental area of the teeth. The slow dissolution of the antimicrobial agent ensures that effective levels of medication are attained for sustained periods, thereby reducing bacterial activity. Examples of making such floss are well known and are disclosed for example in U.S. Pat. No. 5,603,921 herein incorporated by reference.

The present invention also involves a method for treating teeth or gums to reduce plaque or gingivitis comprising applying to the surface of the teeth and/or gums the compositions of this invention as described above. The compositions can be applied to the teeth and gums by any conventional means such as brushing, spraying, painting or rinsing of the oral cavity and the like. The compositions not only cleans and brightens the teeth and retards plaque accumulation, but has been demonstrated to remove pre-existing plaque as well. Additionally, the compositions show a prolonged effect on plaque accumulation following cessation of treatment for at least about one week after use. This property is especially useful in veterinary applications where animals are not necessarily treated on a daily basis, but where longer intervals of time occur between treatments.

The compositions of this invention are also useful as a topical antiseptic, disinfectant or antibacterial which is applied externally to the skin around the mouth or oral cavity. The composition can be delivered in form of a cream, lotion, lip balm, lipstick, or other art-known forms of carriers.

Other uses and applications for compositions prepared according to the present invention will be apparent to those skilled in the art. Preferred uses include, but are not limited to, formulations for oral use such as a mouthwash or dentifrice, mouth rinses (including swish and swallow preparations). Other preferred formulations for topical use are contemplated which include, but are not limited to, skin sanitizers, surgical scrubs and preparations, handwashs and towlettes; formulations for treatment of infections of the skin or mouth area in a human; veterinary medicament for animal skin, hooves, claws, fur, or teeth; nail paints and polishes; skin preparations; and footwear inserts.

The following examples are presented to further illustrate this invention. The examples are intended in an illustrative sense and not in a limitative sense. The present invention includes the embodiments described and shown and any equivalents thereof. All parts and percentages are on a weight basis unless otherwise indicated.

EXAMPLE 1

| Tooth Paste | |
|---|---|
| Abrasive Powder | 12.9 |
| Calcium phosphate | 25.0 |
| Acetic acid | 1.0 |
| Carrageenan | 1.0 |
| Glycerin | 10.0 |
| Sorbitol | 15.0 |
| Sodium lauryl sulfate | 2.0 |
| Flavor | 1.0 |
| Sodium saccharinate | 0.1 |
| Silicon dioxide | 2.0 |
| Water | 30.0 |

EXAMPLE 2

| Tooth Powder | |
|---|---|
| Abrasive powder | 95.3 |
| Sodium lauryl sulfate | 2.0 |
| Acetic acid | 1.0 |
| Flavor | 1.5 |
| Sodium saccharinate | 0.2 |

EXAMPLE 3

| Wet Tooth Powder | |
|---|---|
| Abrasive powder | 64.38 |
| Calcium phosphate | 10.0 |
| Sorbitol | 10.0 |
| Sodium lauryl sulfate | 2.0 |
| Acetic acid | 1.0 |
| Flavor | 1.5 |
| Calcium phosphate | 1.0 |
| Water | 10.0 |
| Sodium saccharinate | 0.12 |

EXAMPLE 4

| Mouthwash | |
|---|---|
| Acetic acid | 1.0 |
| Nonionic surfactant | 0.7 |
| Sorbitol solution | 50.0 |
| Ethanol (95% in water) | 10.0 |
| Coloring agent | 0.0004 |
| Flavoring agent | 0.15 |
| Water | to 100% |

EXAMPLE 5

| Dentifrice | |
|---|---|
| Acetic acid | 3.0 |
| Sodium fluoride | 0.24 |
| Hydrated silica | 10–50 |
| Xylitol | 10–40 |
| Xanthan gum | 0.1–1.5 |
| Cocobetaine | 0.1–1.5 |
| Flavoring agent | 0.9 |
| Water | to 100% |

EXAMPLE 6

| Oral spray | |
|---|---|
| Citric acid; hydrous | 1.0 |
| Nonionic surfactant | 1.2 |
| Ethanol | 12.0 |
| Glycerol | 20.0 |
| Sweetening agent | 0.01 |
| Flavoring agent | 0.10 |
| Water | to 100% |

EXAMPLE 7

| Chewing Gum (per stick) | |
|---|---|
| Estergum | 142 mg |
| Coumarone Resin | 213 mg |
| Latex | 71 mg |
| Paraffin Wax | 47 mg |
| Sorbitol | 1309 mg |
| Corn Syrup | 400 mg |
| Flavoring | q.s. |
| Sodium Bicarbonate | 0.2–43 mg |
| Sodium Chloride | 0.3–23 mg |
| Sodium Thiocyanate | 0.4–32 mg |
| Sodium Fluoride | 0.2–16 mg |
| Ascorbic Acid | 10 mg |
| Acetic Acid | 10 mg |

EXAMPLE 8

| Breath freshener tablet | |
|---|---|
| Wintergreen Oil | 0.6 mg |
| Talc | 10.0 mg |
| Menthol | 0.85 mg |
| Peppermint Oil | 0.3 mg |
| Sodium Saccharin | 0.3 mg |
| Mannitol USP | 180.95 mg |
| Sodium Stearate | 2.0 mg |
| Sodium Bicarbonate | 0.2–43 mg |
| Sodium Chloride | 0.3–23 mg |
| Sodium Thiocyanate | 0.4–32 mg |
| Sorbitol USP | 180.0 mg |
| Lactose USP | q.s. 1 gm |
| Sodium Flouride | 0.2–16 mg |
| Acetic acid | 2 mg |

EXAMPLE 9

| Chewable multivitamin tablet | |
|---|---|
| Vitamin A | 5000 USP units |
| Vitamin D | 400 USP units |
| Ascorbic Acid | 60 mg |
| Thiamine HCl | 1 mg |
| Riboflavin | 1.5 mg |
| Pyridoxine HCl | 1 mg |
| Cyanocobalamin | 2 mcg |
| Calcium Pantothenate | 3 mg |
| Niacinamide | 10 mg |
| Mannitol | 236 mg |
| Corn Starch | 16.6 mg |
| Sodium Saccharin | 1.1 mg |

-continued

| Chewable multivitamin tablet | |
|---|---|
| Sodium Stearate | 6.6 mg |
| Talc | 10 mg |
| Wintergreen Oil | 1.2 mg |
| Menthol | 1.7 mg |
| Peppermint Oil | 0.6 mg |
| Sodium Bicarbonate | 0.2–43 mg |
| Sodium Chloride | 0.3–23 mg |
| Sodium Thiocyanate | 0.4–32 mg |
| Sodium Fluoride | 0.2–16 mg |
| Acetic acid | 22 mg |

EXAMPLE 10

| Veterinary, e.g., dog, tooth gel | |
|---|---|
| Water | 65.95 |
| SD Alcohol 40-B | 18.00 |
| Sorbitol | 10.00 |
| PVM/MA Decadiene Crosspolymer | 1.80 |
| Acetic acid | 1.00 |
| C11–15 Pareth-12 | 1.00 |
| Flavor | 0.50 |
| Methylparaben | 0.20 |
| Lactose (and) Cellulose (and) Hydroxypropyl Methylcellulose (and) Chromium Hydroxyde Green (and) Tocopheryl Acetate | 0.10 |
| Lactose (and) Cellulose (and) Hydroxypropyl Methylcellulose (and) Ultramines (and) Tocopheryl Acetate (and) Retinyl Palmitate | 0.10 |
| Lactose (and) Cellulose (and) Hydroxypropyl Methylcellulose (and) Iron Oxide and Tocopheryl Acetate | 0.10 |
| Triethanolamine | 1.10 |
| Sodium Benzoate | 0.10 |
| Sodium Hexametaphosphate | 0.05 |

EXAMPLE 11

A solution of 0.1% of Neutral Red is applied to the front teeth of each of two male adults A and B who had been using conventional commercially available dentifrice. Thereafter, a similar dyeing operation is conducted one day after they began to use the dentifrice of Example 1 and the plaque-stained areas before and after the use of the dentifrice of Example 1 is compared. In the case of A, the stained area after the change is about only 10% of the initial stained area indicating that the decontamination of the plaque area is about 90%. In the case of B the decontamination of the plaque area is about 50% superior to conventional dentifrice. These beneficial effects result from the twice-daily application of about 5 to 25 gram of the dentifrice of Example 1. Similar beneficial results are obtained when a third subject rinsed the mouth with about 50 to 100 ml of mouthwash of Example 4.

EXAMPLE 12

Minimum inhibitory concentration studies are performed using the gram-negative enterobacterium *Pseudomonas aerugenosa* (American Type Culture Collection #9027) in accordance with the protocol for testing the bactericidal activity of antimicrobial agents (Document M26-T of the National Center for Clinical and Laboratory Standards). *P. aeruienosa* is cultured overnight at 37° C. in trypsin soy broth to a final density of approximately 1×10$^8$ cfu/ml (0.5 McFarland standard) and then diluted 1:10 with cation-adjusted Mueller-Hinton medium. 10 microliters of this bacterial culture is then added to 200 microliters of an already-prepared dilution series of the test solution (Composition of Example 4). After a 5 minute incubation at room temperature, 10 microliters of wash test solution is plated onto a sector of a Letheen-agar plate and incubated at 37° C. overnight. MIC breakpoint is interpreted as the highest dilution for which no growth is evident. The results show that Compositions of Example 4 are far more effective in vitro at inhibiting the growth of *P. aerugenosa* than the control solution, which contains the USP benzalkonium chloride mixture.

The invention has been described with respect to certain preferred embodiments but it will be understood that variations and modifications may be made therein without departing from the spirit of this invention and the scope of the appended claims.

What is claimed is:

1. In a method of removing pre-existing plaque, retard plaque accumulation, clean and brighten teeth of animals and to obtain the useful prolonged effect on plaque accumulation in animals imparted by sodium hexametaphosphate by itself alone, following cessation of treatment for at least about one week in veterinary applications, where animals are not necessarily treated in a daily basis, and have longer intervals of time between treatments the improvement over sodium hexametaphosphate, by itself, alone, comprising applying to the surface of the teeth and/or gums of animals in need thereof, at intervals longer than daily basis treatment, a dental tooth gel consisting essentially of about 1% acetic acid and about 0.05% sodium hexametaphosphate.

2. A method of treating animals for plaque accumulation comprising applying a dental tooth gel comprising acetic acid and sodium hexametaphosphate to the surfaces of the teeth and/or gums of animals in need thereof.

3. The method of claim 2, wherein the tooth gel comprises about 1% acetic acid and about 0.05% sodium hexametaphosphate.

4. The method of claim 2, wherein the tooth gel consists essentially of about 1% acetic acid and about 0.05% sodium hexametaphosphate.

* * * * *